(12) United States Patent
Cowe et al.

(10) Patent No.: US 9,579,464 B2
(45) Date of Patent: Feb. 28, 2017

(54) INJECTION DEVICES

(75) Inventors: Toby Cowe, Oxford (GB); Jeremy Marshall, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 191 days.

(21) Appl. No.: 13/879,448

(22) PCT Filed: Oct. 11, 2011

(86) PCT No.: PCT/GB2011/051950
§ 371 (c)(1),
(2), (4) Date: Jul. 10, 2013

(87) PCT Pub. No.: WO2012/049484
PCT Pub. Date: Apr. 19, 2012

(65) Prior Publication Data
US 2013/0281933 A1    Oct. 24, 2013

(30) Foreign Application Priority Data

Oct. 14, 2010  (GB) .................................. 1017363.1

(51) Int. Cl.
*A61M 5/315*    (2006.01)
*A61M 5/20*     (2006.01)
*A61M 5/32*     (2006.01)

(52) U.S. Cl.
CPC .......... *A61M 5/31501* (2013.01); *A61M 5/20* (2013.01); *A61M 5/2033* (2013.01);
(Continued)

(58) Field of Classification Search
CPC .... A61M 5/20; A61M 5/2033; A61M 5/3202; A61M 5/3204; A61M 5/321;
(Continued)

(56) References Cited

U.S. PATENT DOCUMENTS 3,712,301 A * 1/1973 Sarnoff ............... A61M 5/2033
604/136
3,742,948 A   7/1973 Post et al.
(Continued)

FOREIGN PATENT DOCUMENTS

EP    0 518 416 A1    12/1992
FR    2 905 273 A1     3/2008
(Continued)

OTHER PUBLICATIONS

British Search Report, dated Dec. 22, 2010, from corresponding British application.
(Continued)

*Primary Examiner* — Laura Bouchelle
*Assistant Examiner* — Justin L Zamory
(74) *Attorney, Agent, or Firm* — Young & Thompson

(57) ABSTRACT

An injection device includes an elongate housing (10); a syringe (12) disposed in the housing and having an internal piston (20) to express a dose from a needle (16) at its front end; a trigger device (52) for, in use, activating the internal piston, and a cap (66) that, in a fitted configuration, fits over at least part of the elongate housing and prevents activation of the trigger device.

13 Claims, 8 Drawing Sheets

(52) U.S. Cl.
CPC ........ *A61M 5/31511* (2013.01); *A61M 5/321* (2013.01); *A61M 5/326* (2013.01); *A61M 5/3202* (2013.01); *A61M 5/3204* (2013.01); *A61M 2005/206* (2013.01); *A61M 2005/2073* (2013.01); *A61M 2005/3247* (2013.01)

(58) Field of Classification Search
CPC .............. A61M 5/3213; A61M 5/5086; A61M 2005/206; A61M 2005/2073; A61M 2005/3247; A61M 2005/3254
USPC .... 604/110, 111, 134–136, 164.08, 192–198
See application file for complete search history.

(56) References Cited

U.S. PATENT DOCUMENTS

| | | | |
|---|---|---|---|
| 5,295,965 | A | 3/1994 | Wilmot |
| 5,599,309 | A | 2/1997 | Marshall et al. |
| 7,771,397 | B1 * | 8/2010 | Olson ............................ 604/192 |
| 7,976,514 | B2 | 7/2011 | Abry et al. |
| 2007/0191758 | A1 | 8/2007 | Hunter et al. |
| 2008/0009807 | A1 | 1/2008 | Hommann |
| 2009/0209939 | A1 * | 8/2009 | Verespej et al. ............... 604/506 |
| 2011/0054411 | A1 * | 3/2011 | Dowds et al. ................. 604/198 |
| 2011/0092915 | A1 * | 4/2011 | Olson et al. ................... 604/198 |

FOREIGN PATENT DOCUMENTS

| | | |
|---|---|---|
| GB | 686343 A | 1/1953 |
| WO | 00/15280 A1 | 3/2000 |
| WO | 03/039635 A2 | 5/2003 |
| WO | 2006/045215 A1 | 5/2006 |
| WO | 2006/129196 A1 | 12/2006 |
| WO | 2007/114934 A2 | 10/2007 |
| WO | 2008/008206 A1 | 1/2008 |
| WO | 2008/029280 A2 | 3/2008 |
| WO | 2009/007229 A1 | 1/2009 |
| WO | 2009/063030 A1 | 5/2009 |

OTHER PUBLICATIONS

British Search Report, dated Feb. 2, 2011, from corresponding British application.
International Search Report, dated Aug. 28, 2012, from corresponding PCT application.

* cited by examiner

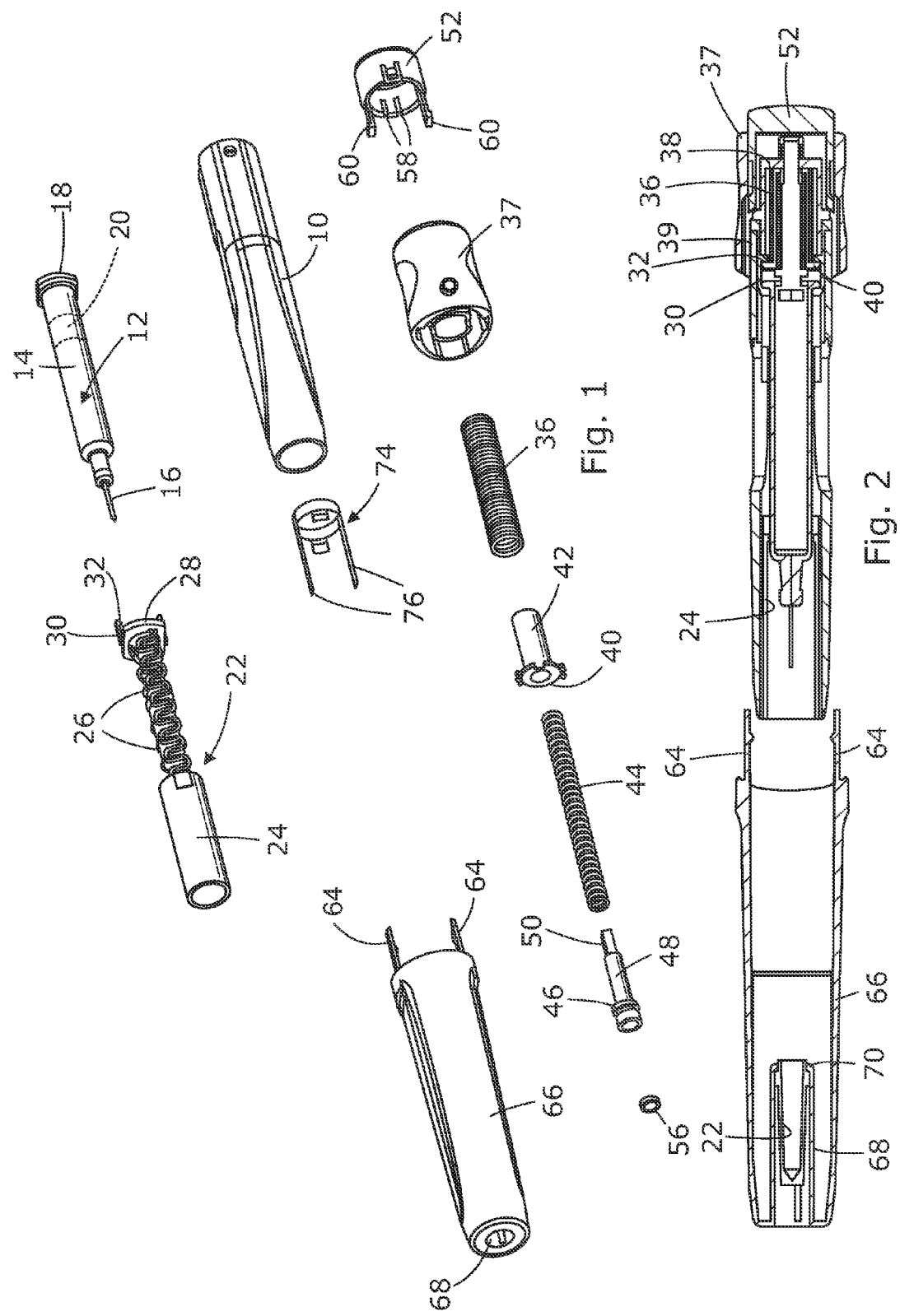

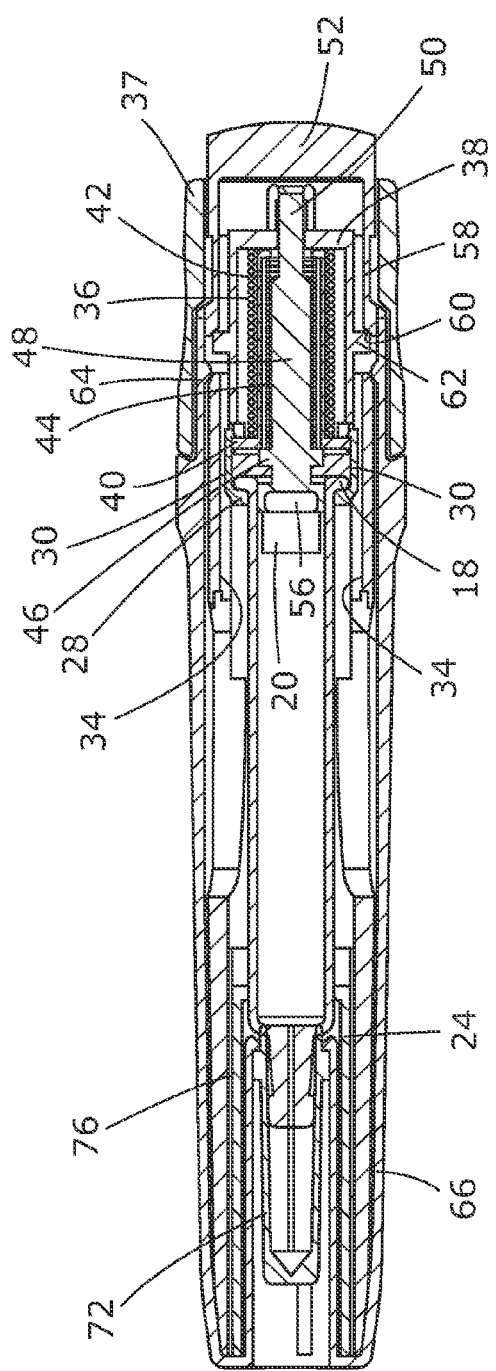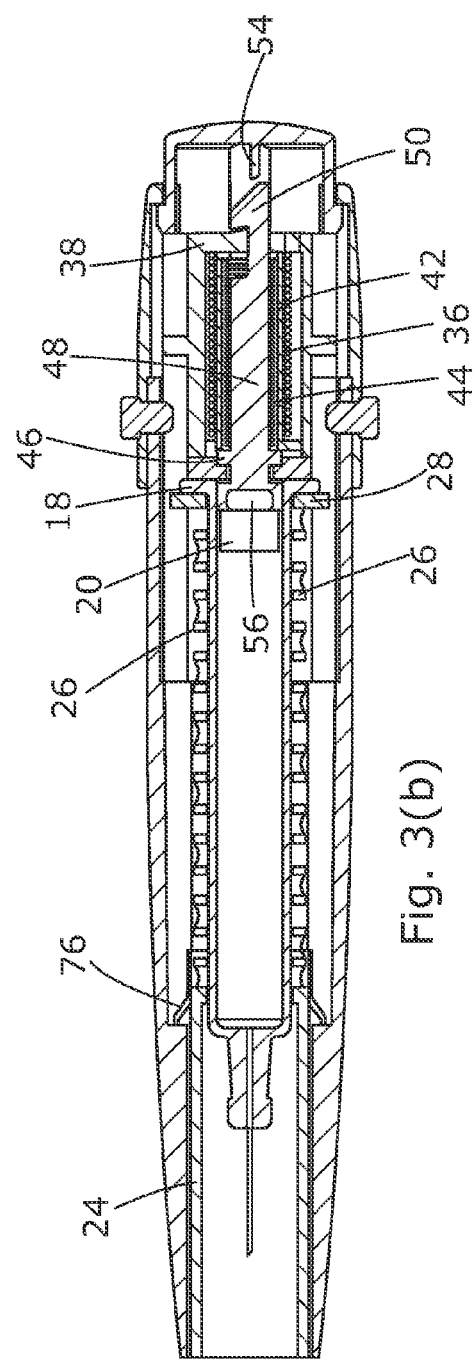

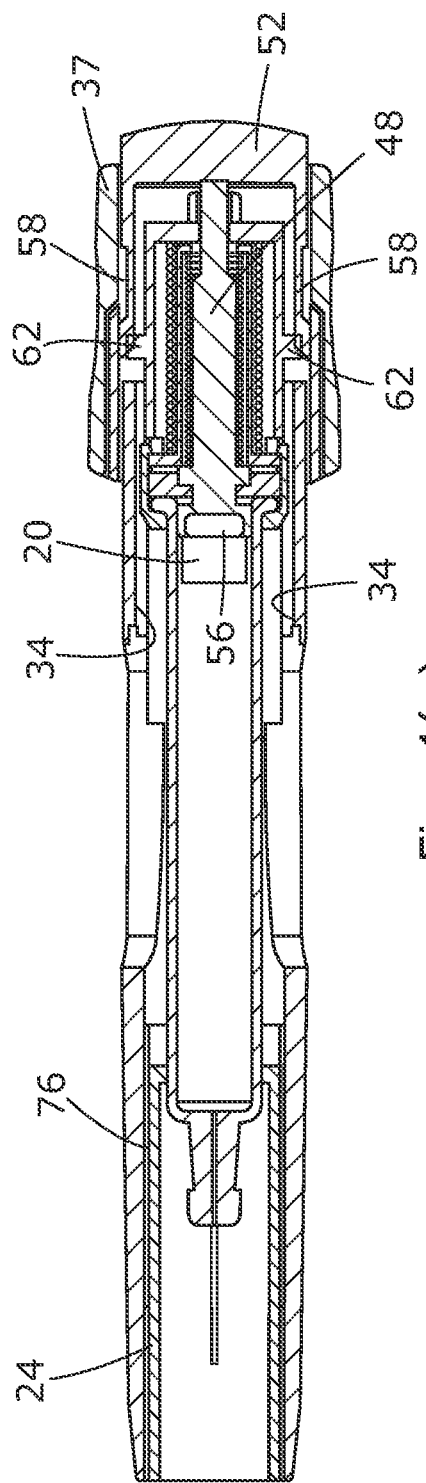
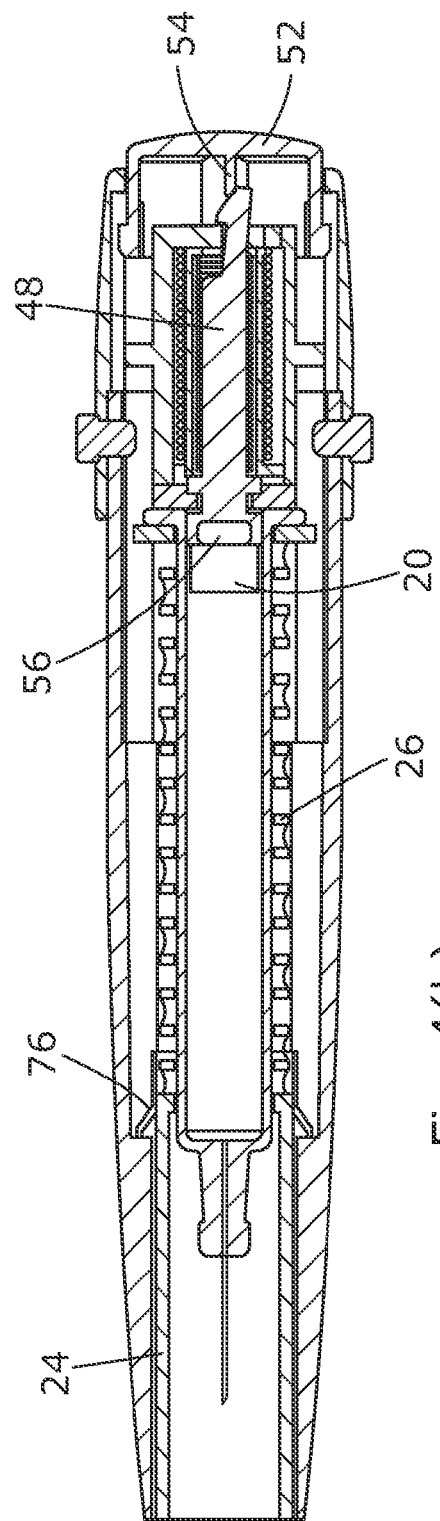
Fig. 4(a)
Fig. 4(b)

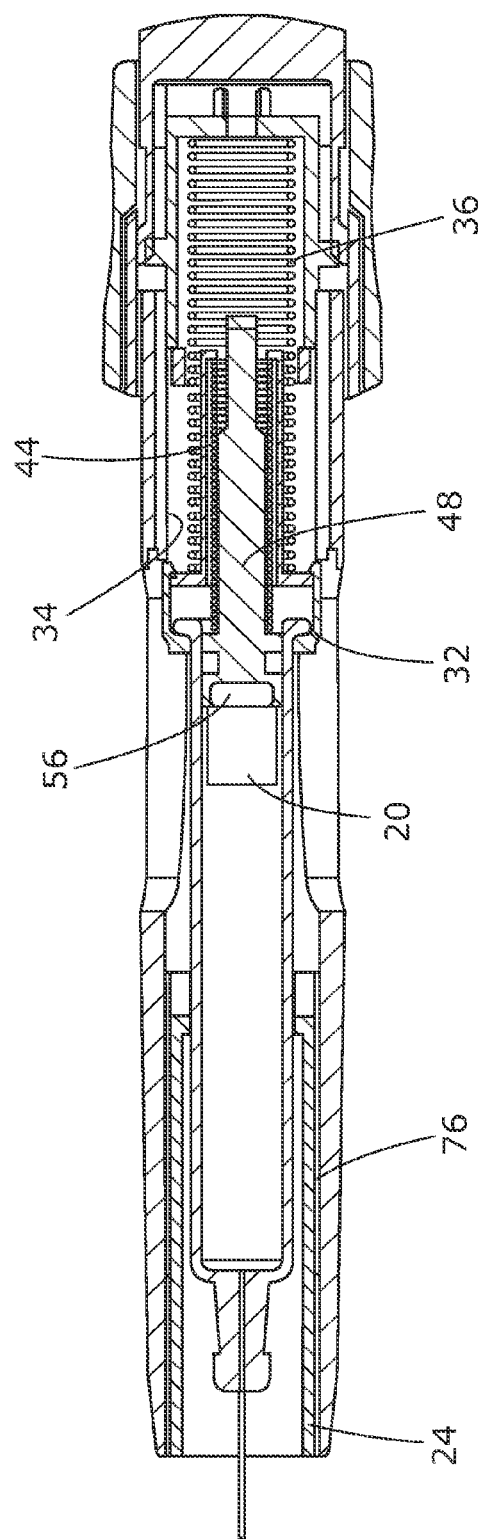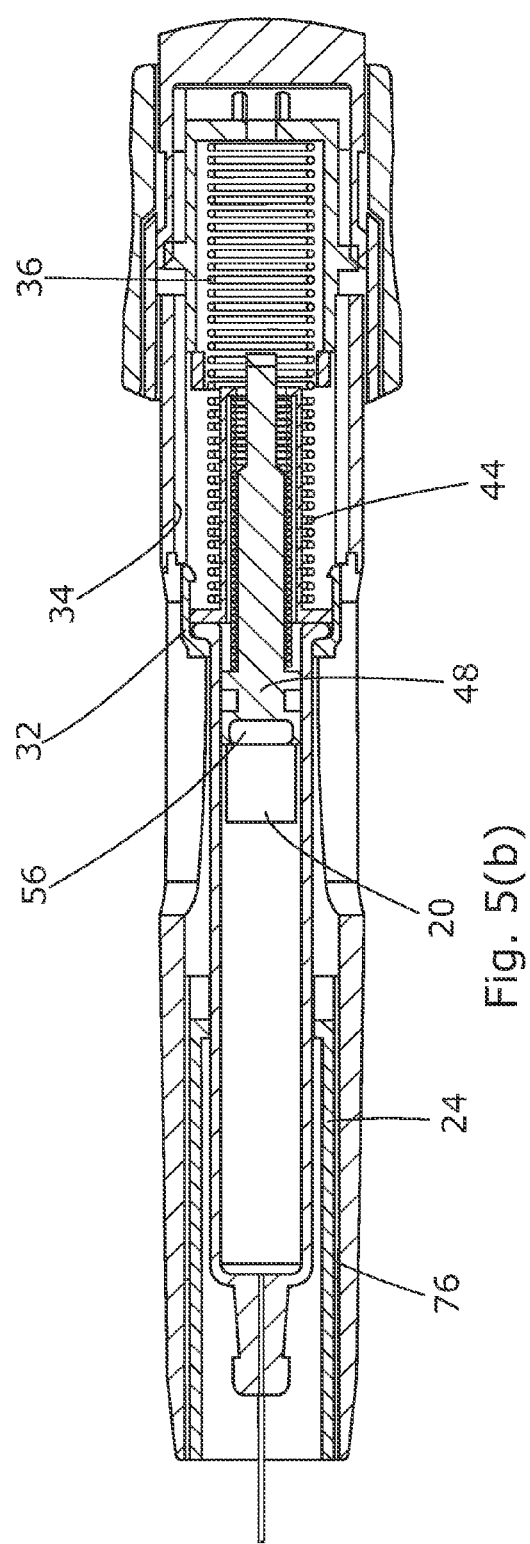

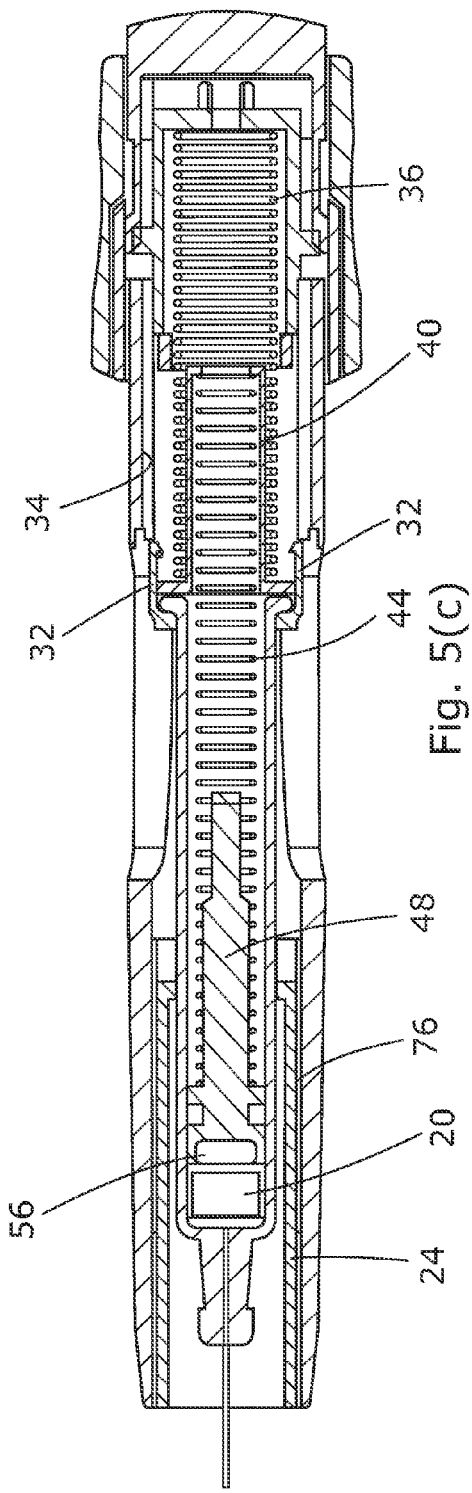
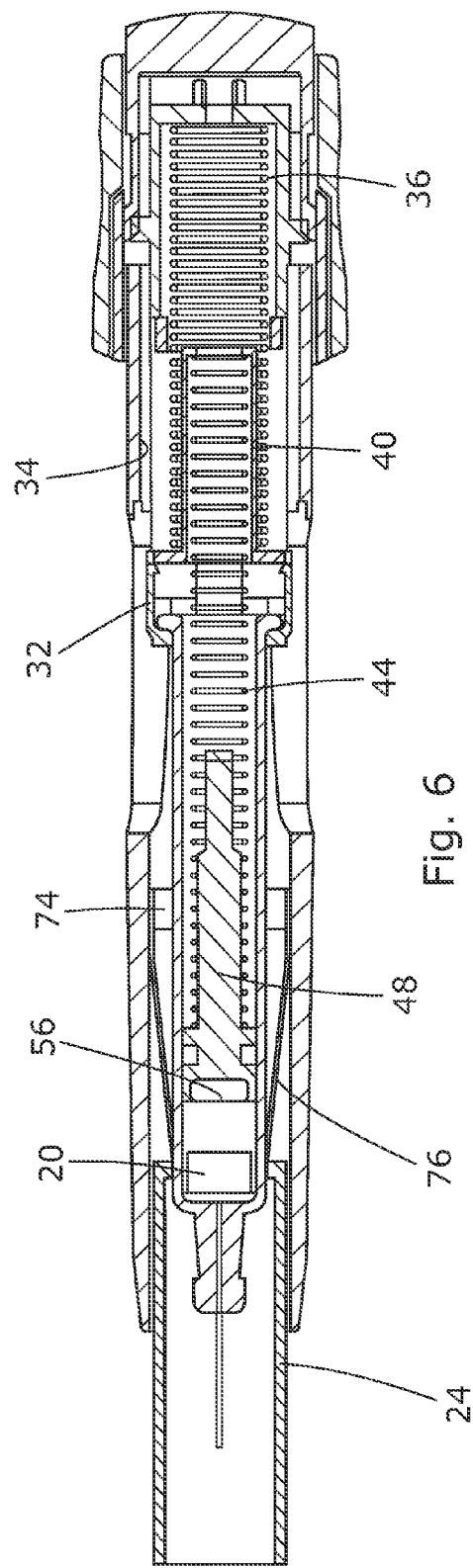

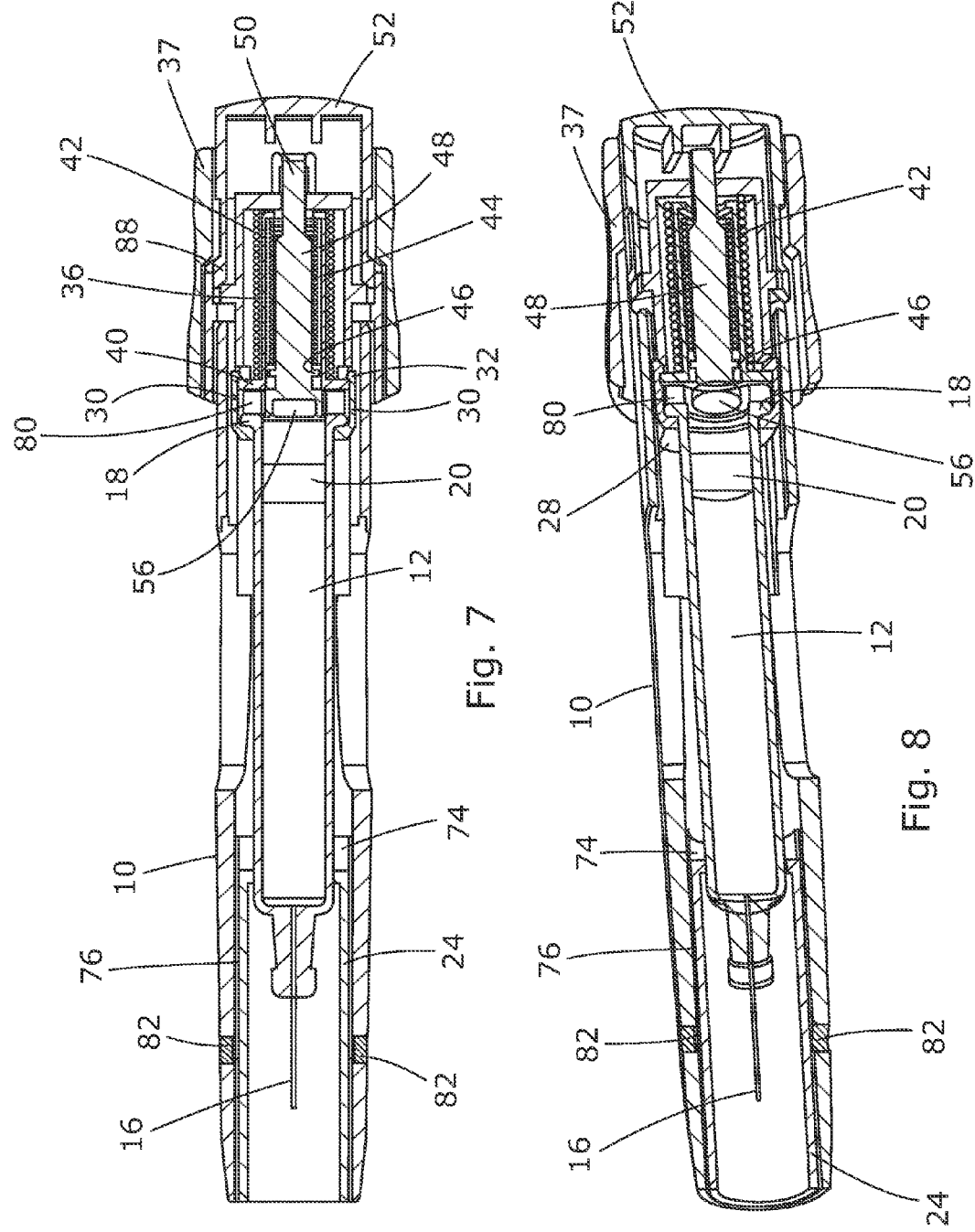

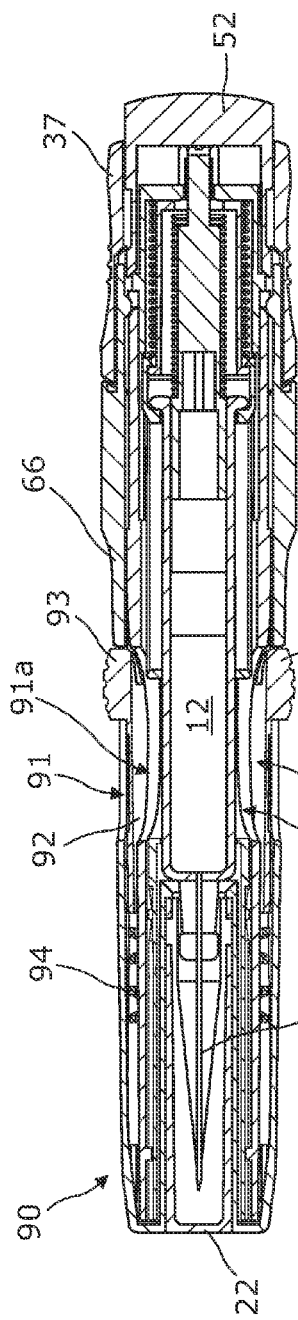
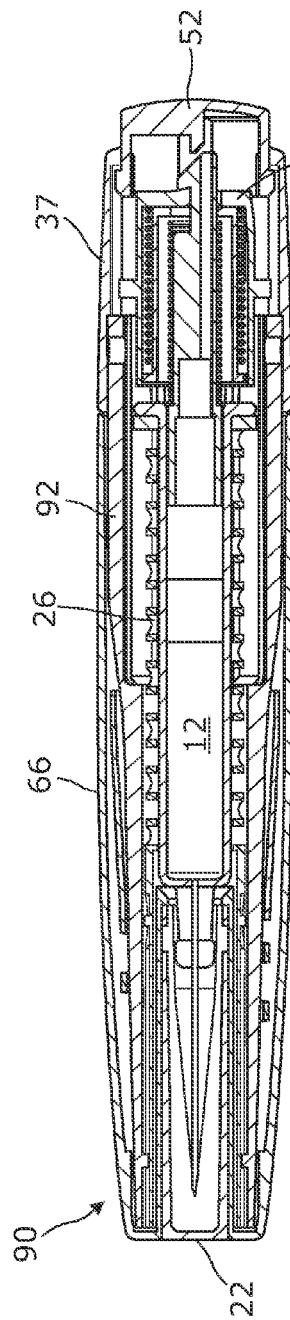
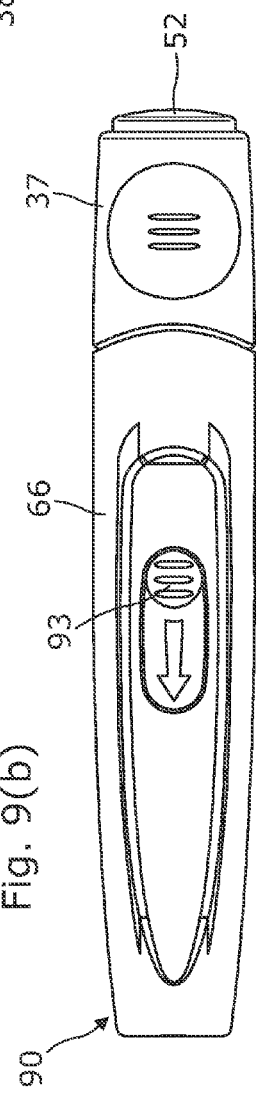
Fig. 9(a)
Fig. 9(b)
Fig. 9(c)

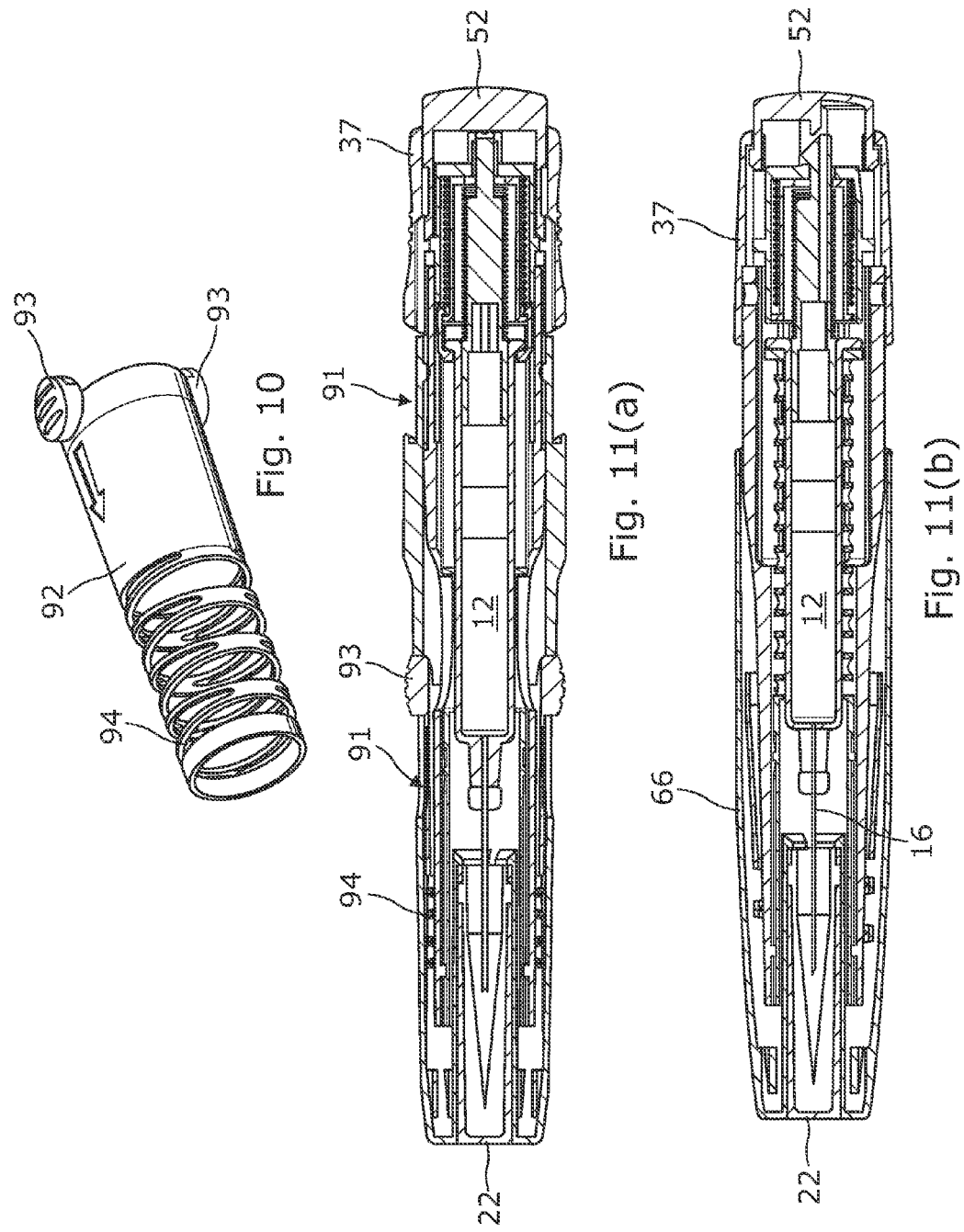

INJECTION DEVICES

This invention relates to injection devices.

It is important that the needles of injection devices remain covered when not in use for reasons of safety. Known autoinjector devices typically include a trigger button that is pressed to deploy the needle. Although convenient to use, unintentional pressing of the button could result in a person being accidentally injected with a drug that may be harmful to him/her.

Conventional injection devices also typically include a solid body that does not allow visual inspection of the contents of the syringe. However, some drugs are photosensitive and so it is not desirable for the bodies of injection devices to be fully transparent.

Embodiments of the present invention are intended to address at least some of the abovementioned problems.

Accordingly, in one aspect, this invention provides an injection device including:

an elongate housing;

a syringe disposed in said housing and having an internal piston to express a dose from a needle at its front end;

a trigger device for, in use, activating the internal piston, and a cap that, in a fitted configuration, fits over at least part of the elongate housing and prevents activation of the trigger device.

The trigger device may be slidably mounted within the housing and the cap can includes at least one arm that, in the fitted configuration, prevents sliding of the trigger device in an activation direction. The trigger device may projects rearwardly from a rear end of the housing. The trigger device may be biased against the activation direction. The trigger device can be biased by means of at least one sprung member. The at least one sprung member can include a cam surface which, in use when sliding in the activation direction, rides over an abutment inside the housing. The at least one arm, when the cap is in the fitted configuration, can prevent the cam surface of the sprung member from riding over the abutment. The injection device may further include a rear collar that fits over a rear portion of the housing and the at least one arm, when the cap in the fitted configuration, may be located inside a channel defined between an inner surface of the collar and an outer surface of the rear portion of the housing, thereby restricting movement of the at least one sprung arm.

The injection device may further include a shield for the needle and the cap may further include an arrangement that removes the needle shield when, in use, the cap is removed. The needle shield may be supported within an interior arrangement of the cap. The interior arrangement can include a re-entrant cylindrical portion. The arrangement for removing the needle shield can include at least one claw feature that, in use when the cap is removed from the housing, pulls the needle shield away from the syringe.

The cap may further include:

at least one aperture, that, when the cap is in its fitted configuration is aligned with an aperture in the housing located above a portion of the syringe, and a shield arrangement configured to move between a closed configuration that blocks the at least one cap aperture and an open configuration that at least partially exposes the at least one cap aperture.

A biasing arrangement may bias the shield arrangement to the closed configuration. The shield arrangement can include a portion with at least one solid wall slidably mounted within the cap, the solid wall being aligned with the aperture when the shield is in its closed configuration. The housing can further include at least one aperture, where the at least one aperture of the cap, when the cap is its fitted configuration, is aligned with the at least one housing aperture. The cap can have two diametrically-opposed elongate said apertures.

Whilst the invention has been described above, it extends to any inventive combination set out above, or in the following description or drawings.

The invention may be performed in various ways, and two embodiments thereof will now be described by way of example only, reference being made to the accompanying drawings, in which:

FIG. 1 is an exploded view of the first embodiment of an autoinjector in accordance with this invention;

FIG. 2 is a side section view through the autoinjector of FIG. 1 assembled and prior to use;

FIGS. 3(a) and (b) are respective side and top section views of the autoinjector with the cap in place, and removed;

FIGS. 4(a) and (b) are respective side and top section views of the autoinjector with the firing button partially depressed immediately prior to the release of the plunger;

FIGS. 5(a), (b) and (c) are respective side section views showing the autoinjector with the syringe in its forwardmost position, shortly after breakout of the piston, and at the injection complete stage, respectively;

FIG. 6 is a view of the autoinjector after use, with the shroud extended and locked out by the magnetically enabled latch;

FIG. 7 is a side view through a second embodiment of an autoinjector (without its cap);

FIG. 8 is a shaded side view of FIG. 7;

FIGS. 9(a) and (b) are respective side and top section views of a third embodiment of the autoinjector with a cap in its fitted configuration;

FIG. 9(c) is a plan view of the second embodiment with the cap in its fitted configuration;

FIG. 10 shows a light shield feature of the second embodiment, and

FIGS. 11(a) and (b) are respective side and top section views of the second embodiment with the cap partly removed.

Referring initially to FIGS. 1 to 3, the autoinjector comprises an outer housing 10 of cylindrical form in the bore of which is disposed a syringe 12 of known form with a barrel 14, a needle 16 extending from the forward end, and a flange 18 at its rear end. A medicament is contained within the syringe and can be expressed through the needle by a piston 20 inside the barrel. The syringe is supported and surrounded by moulded plastics shroud/carrier 22 assembly comprising a forward hollow cylindrical portion 24 integrally formed with diametrically opposed springs 26 to either side, and a collar 28 adapted to engage the forward face of the syringe flange. Extending rearwardly from the collar are two diametrically opposed clearance fingers 30 with barbed teeth 32 that engage the intermediate member, as to be described below. In the pre-use position as shown in FIG. 3(a), the barbed fingers are prevented from outward splaying movement by the base of respective diametrically opposed grooves 34 on the inner surface of the rear part of the housing. In the pre-use position, the shroud portion 24 is telescopically received within the forward end of the housing and co-terminous therewith.

In the rear of the housing is provided a drive mechanism which comprises a first outer spring 36 which acts between the front face of a transverse inner wall 38 at the rear of the housing and a forward flange 40 of a top hat-shaped intermediate member 42. An inner, second, spring 44 is received within a cylindrical part of the intermediate member 42 and acts between an inner face of the rear end wall thereof and a circumferential rib 46 on the forward part of a plunger 48. At the rear end, the plunger has a resilient hooked arm 50 (see FIGS. 1, 3(b)) which latches around the edge of an aperture in the transverse inner wall 38 of the housing. Projecting rearwardly from the rear end of the housing is a captive axially slideable trigger button 52 movable against a rearward bias from the position shown in e.g. FIG. 3(b), where a release finger 54 is spaced rearwardly of the hooked arm 50, to a forward portion where the finger 54 cams the hooked arm to release its retention by the wall 38, thereby allowing the springs 36, 44 to drive the plunger 48 forwardly. The plunger is shaped and sized so that it can pass into and down the internal bore of the syringe barrel 14, to urge the piston 20 to express a dose. In the forward end of the plunger is a cylindrical recess in which is located a small powerful magnet 56.

The trigger button 52 is biased rearwardly by means of two integral forwardly extending sprung arms 58 with cam surfaces 60 which ride over respective abutments 62 inside the rear of the housing. However, initially, forward movement of the trigger button is prevented by means of two rearwardly extending locking arms 64 which extend back from the rear end of a cap 66. A rear collar 37 is fitted over the rear portion of the housing 10, out of which the button 52 protrudes rearwardly. When the cap is in its fitted configuration, the locking arms 64 are located inside an annular channel 39 defined between an inner surface of the collar and an outer surface of the rear portion of the housing. In its fitted configuration, the cap covers the whole of the forward end of the housing and has a re-entrant cylindrical portion 68 with claw features 70. The claw features 70 slip over the rear end of a needle shield 72 which is secured to the front end of the needle during manufacture. Thus the cap 66 fulfils the functions of acting as a safety catch for the trigger button 52, serving as a shield remover. Anchored inside the forward end of the housing is a latch 74 formed of pressed steel or other ferro-magnetic material to provide two latch arms 76 which extend forwardly from an anchorage normally to sit in an annular space between the shroud 24 and an inner part of the housing wall.

In operation, the user pulls the cap 66 off forwardly which removes the needle shield 22 from the syringe and arms the device by rendering the trigger button 52 operational. The user then offers the injection device up to the injection site and presses the trigger button 52. This releases the hooked arm 50 of the plunger 48 as shown more particularly in FIG. 4(b). Once the plunger is released, the first spring 36 expands to extend the syringe 20 so that the needle penetrates the flesh. During this period (FIG. 5(a)), the second spring 44 remains substantially fully compressed, with the plunger 48 bearing against the piston 20 within the syringe but not moving it relative to the syringe. During the initial phase of penetration, the clearance fingers 32 on the syringe supporting collar 28 are constrained against outward splaying movement by the grooves 34 and so a gap is preserved between the syringe flange 18 and the flange 40 of the intermediate member 42, as long as the fingers are still in engagement with the constraining grooves.

It will be appreciated that many variations of the cap and trigger button blocking mechanisms described above are possible. For instance, the cap may include at least one member other than the arms 64 for blocking/interfering with the sliding motion of the button.

The fingers 32 exit the constraining grooves 34 at about the same time as forward movement of the syringe is arrested by the compression spring portions 26 bottoming out, the shroud 24 being held against movement by contact with the skin surface. When the syringe is arrested, the first spring 36 continues to expand to drive the flange 40 of the intermediate member into engagement with the syringe flange 18 thereby contributing to the force required to initiate movement of the piston down the syringe (FIG. 5(b)). From this position the second spring 44 expands to drive the piston down the barrel of the syringe to express a dose. At the end of its travel, it will be noted that the magnet 56 in the plunger is spaced between the latching arms 76 of the latch 74, as shown in FIG. 5(c). When the dose has been expressed, the user pulls the device away from the flesh and so the shroud portion 24 is free to expand under the influence of the compression spring portions 26. The shroud portion is driven by the springs 26 forwardly beyond the front tips of the latching arms 76. Once this happens, the latching arms are free to move inwardly to the latching positions shown in FIG. 6, under the influence of the magnet 20. The shroud portion 24 is therefore locked out and the device thereby rendered safe.

In other embodiments, not shown, further magnets or ferro-magnet material may be disposed in the front end of the housing around or in front of the syringe in order to provide a magnetic boost effect as the plunger nears the end of its stroke.

Referring now to FIGS. 7 and 8 the second embodiment has many of the same components as the first embodiment and which act in a similar fashion. These components are given the same reference numbers and will not therefore be described in detail again. This second embodiment incorporates a magnetic coupling embodiment between the plunger 48 and the syringe designed so that during an initial penetration phase of movement the plunger is coupled magnetically to a thrust collar 80 of ferro-magnetic material that is positioned in contact with the rear face of the syringe flange 18. Thus the plunger 48 and the syringe 18 are initially held against relative movement and so move as one during this phase, until the syringe is arrested by reaching its forwardmost position, with the needle inserted into the injection site. Upon arrest of the syringe, the spring force acting on the plunger overcomes the magnetic coupling force and the coupling yields so that the plunger is released to move forward relative to the syringe to move the plunger into contact with and to urge the piston forwardly to expel a dose. As previously, as the plunger moves alongside the ferro-magnetic latching arms 76 and they are attracted inwardly. This is enhanced in the embodiment by provision of two magnets 82 on the forward ends of the latching arms. These magnets are aligned so as to be attached towards and to exert a pull on the magnet 56 in the plunger to provide a magnetically influenced forward boost to the plunger toward the forwardmost end of its stroke. Upon completion of the injection and removal of the device from the site, the shroud 24 extends forwardly as the spring portions 26 re-expand, and as a rearward lip on the shroud passes the magnets, the latching arms move inwards to block retraction movement of the shroud and thereby lock it out. The magnets 82 may be housed slideably in through-holes in the housing wall, allowing them also to move inwards with the latching arms as the rearward lip on the shroud passes the magnets, and so provide a visual and tactile confirmation of locking out of the shroud 24.

Referring to FIGS. 9(a), (b) and (c) and 11(b) and (b), a third embodiment 90 of the autoinjector is shown. Components in common with the earlier embodiments have been given the same reference numerals. In this embodiment, the cap 66 includes at least one aperture 91. In the example there are two diametrically-opposed elongate apertures with rounded ends, located around midway along the length of the cap, but it will be appreciated that the number, position and shape of the aperture(s) can vary. The housing 10 also includes at least one corresponding aperture 91a and when the cap is fitted on the shield, the sets of apertures are at least partially aligned.

A light shield 92 is slidably mounted inside the cap 66, over the cylindrical housing 10. In alternative embodiments, the light shield may be slidably mounted on another component of the device and may be accessible through the cap. As can be seen in FIG. 10, the example light shield includes a cylindrical portion with solid walls from which a spring 94 portion extends. A pair of diametrically opposed circular buttons 93 with finger grooves are located at the other end of the cylindrical portion and stand proud of its outer surface. In the position shown in FIG. 9, the cylindrical portion of the light shield covers the apertures, preventing the content of the syringe 20 from being exposed to light. This can be advantageous in the case of photosensitive drugs. A user can use one or both of the buttons 93 to push the light shield downwards, which compresses the plastic spring 94 against an abutment 95 on the inner surface of the cap 66. The user can then check the contents of the syringe through the apertures and when he/she releases the button(s), the shield springs back to the position of FIG. 9(c). Alternatives to the light shield described above are possible, e.g. a hinged lid on the cap.

The invention claimed is:

1. An injection device including:
an elongate housing (10);
a syringe (12) disposed in said housing and having an internal piston (20) to express a dose from a needle (16) at its front end;
a trigger device (52) for, in use, activating the internal piston, wherein the trigger device (52) is slidably mounted within the housing (10) and projects rearwardly from a rear end of said housing (10), the trigger device being biased against the activation direction by means of at least one sprung member, the sprung member including a cam surface (60) which, in use when sliding in the activation direction, rides over an abutment (62) inside the housing (10); and
a cap (66) that, in a fitted configuration, fits over at least part of the elongate housing and directly blocks the trigger device to prevent activation of the trigger device,
wherein the cap includes at least one arm (64) that, in the fitted configuration, directly blocks sliding motion of the trigger device in an activation direction, wherein a rearward surface of the at least one arm abuts a corresponding surface of the trigger device to directly block the sliding motion of the trigger device in the activation direction by blocking outward movement of the corresponding surface of the trigger device, and
wherein, a forward surface of the at least one sprung member (58) is the corresponding surface of the trigger device, and the at least one arm (64), when the cap (66) is in the fitted configuration, prevents the cam surface (60) of the sprung member (58) from moving outward and riding over the abutment (62) by the rearward surface of the at least one arm (64) abutting the forward surface of the at least one sprung member (58).

2. An injection device according to claim 1, further including a rear collar (37) that fits over a rear portion of the housing (10) and wherein the at least one arm (64), when the cap (66) in the fitted configuration, is located inside a channel (39) defined between an inner surface of the collar and an outer surface of the rear portion of the housing, thereby restricting movement of the at least one sprung arm (58).

3. An injection device according to claim 1, further including a shield (72) for the needle (16) and wherein the cap (66) further includes an arrangement (74) that removes the needle shield when, in use, the cap is removed.

4. An injection device according to claim 3, wherein the needle shield (72) is supported within an interior arrangement (68) of the cap (66).

5. An injection device according to claim 4, wherein the interior arrangement includes a re-entrant cylindrical portion (68).

6. An injection device according to claim 4, wherein the arrangement for removing the needle shield (72) includes at least one claw feature (70) that, in use when the cap (66) is removed from the housing (10), pulls the needle shield away from the syringe (12).

7. An injection device including:
an elongate housing (10);
a syringe (12) disposed in said housing and having an internal piston (20) to express a dose from a needle (16) at its front end;
a trigger device (52) for, in use, activating the internal piston; and
a cap (66) that, in a fitted configuration, fits over at least part of the elongate housing and prevents activation of the trigger device,
wherein the cap (66) further includes:
at least one aperture (91), that, when the cap is in its fitted configuration is aligned with an aperture (91a) in the housing (10) located above a portion of the syringe (12), and
a shield arrangement (92) configured to move between a closed configuration that blocks the at least one cap aperture and an open configuration that at least partially exposes the at least one cap aperture.

8. An injection device according to claim 7, wherein a biasing arrangement (94) biases the shield arrangement to the closed configuration.

9. An injection device according to claim 8, wherein the shield arrangement includes a portion (92) with at least one solid wall slidably mounted within the cap, the solid wall being aligned with the aperture (91) when the shield is in its closed configuration.

10. An injection device according to claim 7, wherein the cap (66) has two diametrically-opposed elongate said apertures (91).

11. An injection device according to claim 5, wherein the arrangement for removing the needle shield (72) includes at least one claw feature (70) that, in use when the cap (66) is removed from the housing (10), pulls the needle shield away from the syringe (12).

12. An injection device according to claim 9, wherein the arrangement for removing the needle shield (72) includes at least one claw feature (70) that, in use when the cap (66) is removed from the housing (10), pulls the needle shield away from the syringe (12).

13. An injection device including:

an elongate housing (10);

a syringe (12) disposed in said housing and having an internal piston (20) to express a dose from a needle (16) at its front end;

a trigger device (52) for, in use, activating the internal piston;

a cap (66) that, in a fitted configuration, fits over at least part of the elongate housing and prevents activation of the trigger device, wherein the trigger device (52) is slidably mounted within the housing (10) and the cap (66) includes at least one arm (64) that, in the fitted configuration, prevents sliding of the trigger device in an activation direction, wherein the trigger device (52) projects rearwardly from a rear end of the housing (10), wherein the trigger device (52) is biased against the activation direction, wherein the trigger device (52) is biased by means of at least one sprung member (58), wherein the at least one sprung member (58) includes a cam surface (60) which, in use when sliding in the activation direction, rides over an abutment (62) inside the housing (10), wherein the at least one arm (64), when the cap (66) is in the fitted configuration, prevents the cam surface (60) of the sprung member (58) from riding over the abutment (62); and a rear collar (37) that fits over a rear portion of the housing (10) and wherein the at least one arm (64), when the cap (66) in the fitted configuration, is located inside a channel (39) defined between an inner surface of the collar and an outer surface of the rear portion of the housing, thereby restricting movement of the at least one sprung arm (58).

* * * * *